United States Patent [19]

Seto et al.

[11] Patent Number: 5,660,793
[45] Date of Patent: Aug. 26, 1997

[54] BIOCHEMICAL ANALYSIS SYSTEM

[75] Inventors: Shunichi Seto; Akihiro Komatsu, both of Kanagawa-ken, Japan

[73] Assignee: Fuji Photo Film Co., Ltd., Kanagawa, Japan

[21] Appl. No.: 459,629

[22] Filed: Jun. 2, 1995

Related U.S. Application Data

[63] Continuation of Ser. No. 199,360, Feb. 18, 1994, abandoned, which is a continuation of Ser. No. 15,598, Feb. 10, 1993, abandoned.

[30] Foreign Application Priority Data

Feb. 12, 1992 [JP] Japan ................. 4-025193

[51] Int. Cl.$^6$ .................. G01N 35/04; G01N 35/10
[52] U.S. Cl. .................. 422/64; 436/46; 436/48; 436/49
[58] Field of Search .................. 422/63–67; 436/46–48, 436/49; 220/608, 731, 908

[56] References Cited

U.S. PATENT DOCUMENTS

| | | | |
|---|---|---|---|
| 2,797,136 | 6/1957 | Nelson | 220/908 |
| 3,964,630 | 6/1976 | Getz | 220/908 |
| 4,296,069 | 10/1981 | Smith et al. | 422/64 |
| 4,689,202 | 8/1987 | Khoja et al. | 436/47 |
| 4,826,659 | 5/1989 | Akisada | 422/63 |
| 4,855,109 | 8/1989 | Muraishi et al. | 422/63 |
| 4,928,540 | 5/1990 | Kido et al. | 422/63 |
| 5,075,079 | 12/1991 | Kerr et al. | 436/47 |
| 5,081,038 | 1/1992 | Sugaya et al. | 422/64 |
| 5,102,624 | 4/1992 | Muraishi | 422/64 |
| 5,152,420 | 10/1992 | Bird et al. | 220/908 |
| 5,196,168 | 3/1993 | Muszak et al. | 422/64 |

FOREIGN PATENT DOCUMENTS

| | | |
|---|---|---|
| 498696 | 8/1992 | European Pat. Off. |
| 61-26864 | 2/1986 | Japan . |
| 1602378 | 11/1981 | United Kingdom . |

Primary Examiner—Jill Warden
Assistant Examiner—Jan M. Ludlow
Attorney, Agent, or Firm—Sughrue, Mion, Zinn, Macpeak and Seas

[57] ABSTRACT

A biochemical analysis system includes a depositing mechanism which deposits a sample liquid on a chemical analysis slide having a reagent layer, an incubator which incubates the chemical analysis slide with the sample liquid at a predetermined temperature for a predetermined time, a transfer mechanism which loads the slide in the incubator and removes it therefrom, and an optical density measuring system which measures the optical density of the chemical analysis slide after incubation and determines the concentration of a specific biochemical component in the sample liquid through the optical density of the chemical analysis slide. The incubator has a rotary body in which a slide discarding hole is formed at the center thereof and a plurality of slide holding portions are formed to extend from the outer peripheral surface of the rotary body toward the center of the rotary body and communicate with the slide discarding hole. The transfer mechanism inserts the chemical analysis slides into the respective slide holding portions by moving each slide toward the center of the rotary body and drops the slides into the discarding hole after measurement by moving the slides further toward the center of the rotary body.

7 Claims, 5 Drawing Sheets

CONVENTIONAL DEVICE

BIOCHEMICAL ANALYSIS SYSTEM

This is a Continuation of application Ser. No. 08/199,360 filed Feb. 18, 1994, now abandoned, which in turn is a Continuation of application Ser. No. 08/015,598, filed Feb. 10, 1993, now abandoned.

BACKGROUND OF THE INVENTION

1. Field of the Invention

This invention relates to a biochemical analysis system which deposits a sample liquid such as blood, serum, urine or the like on a chemical analysis slide having thereon a reagent layer whose optical density changes by chemical reaction with a specific biochemical component contained in the sample liquid and determines the concentration of the specific biochemical component in the sample liquid by measuring the optical density of the slide.

2. Description of the Prior Art

There has been put into practice a biochemical analysis system using a dry-type chemical analysis slide with which a specific component contained in a sample liquid can be quantified through a droplet of the sample liquid deposited on the slide. When chemical components or the like contained in a sample liquid is analyzed using such a dry-type chemical analysis slide, a droplet of the sample liquid is deposited on the slide and is held at a constant temperature for a predetermined time in an incubator so that coloring reaction occurs, and the optical density of the color formed by the coloring reaction is optically measured. That is, measuring light containing a wavelength which is preselected according to the combination of the component to be analyzed and the reagent contained in the reagent layer of the slide is projected onto the slide and the optical density of the slide is measured. Then the component to be analyzed is quantified on the basis of the optical density using a calibration curve which represents the relation between the concentration of the biochemical component and the optical density.

In such a biochemical analysis system, the chemical analysis slides are transferred to the incubator one by one and then removed from the incubator after measurement. As disclosed, for instance, in Japanese Unexamined Patent Publication No. 61(1986)-26864 and U.S. Pat. No. 4,296,069, conventionally the chemical analysis slides are loaded in the incubator from the outer peripheral side of the disk-like rotary incubator and then removed therefrom by pushing them from the inside of the incubator toward the outer peripheral side or taking them out from the outer peripheral side.

However in any of the conventional systems, loading and removal of the chemical analysis slide must be effected in separate positions and accordingly the mechanism for loading and removal of the chemical analysis slide is complicated in structure.

That is, a mechanism for depositing the sample liquid and a slide holding means which holds virgin chemical analysis slides are provided adjacent to the loading position where the chemical analysis slide is loaded in the incubator, and accordingly the chemical analysis slide which has finished with measurement cannot be taken out in the loading position and must be taken out in a separate position. Thus the mechanism for loading the chemical analysis slide and the mechanism for taking out the same must be separately provided, which complicates the mechanism for loading and removal of the chemical analysis slide.

Further any trouble in transferring the chemical analysis slide can give rise to a problem that the reagent layer of the chemical analysis slide cannot react with a sample liquid deposited thereon for a predetermined time at a predetermined temperature, which results in deterioration of the measuring accuracy. Thus it is important to surely load and remove the chemical analysis slide without trouble in order to ensure the measuring accuracy, thereby improving the reliability of the analysis. The complicated mechanism for loading and removal of the chemical analysis slide is disadvantageous from the viewpoints of both the reliability and the cost.

SUMMARY OF THE INVENTION

In view of the foregoing observations and description, the primary object of the present invention is to provide a biochemical analysis system in which the chemical analysis slide can be surely loaded in and removed from an incubator with a simple mechanism, thereby ensuring a high reliability of the analysis.

In the biochemical analysis system in accordance with the present invention, the incubator has a rotary body in which a slide discarding hole is formed at the center thereof and a plurality of slide holding portions are formed to extend from the outer peripheral surface of the rotary body toward the center of the rotary body and communicate with the slide discarding hole and the transfer mechanism inserts the chemical analysis slides into the respective slide holding portions by moving each slide toward the center of the rotary body and drops the slides into the discarding hole after measurement by moving the slides further toward the center of the rotary body.

Preferably a discard box for recovering the used slides is disposed below the discarding hole and a projection is provided in the discard box to disperse the slides dropping into the discard box. Further a tip drawing means which removes the nozzle tip from the depositing means is preferably provided in the vicinity of the incubator and the nozzle tips removed from the depositing means are recovered in the discard box together with the used slides.

In the biochemical analysis system in accordance with the present invention, the transfer mechanism inserts the chemical analysis slides into the incubator by linearly moving them and the chemical analysis slides are removed from the incubator after measurement by the same transfer mechanism which linearly moves them further toward the center of the incubator and drops them into the discarding hole. Accordingly loading and removal of the chemical analysis slides can be effected by the same transfer mechanism. Further since the slides are transferred along a linear path, the transfer mechanism may be simple in structure and transfer of the slides can be effected with high reliability.

Further, by recovering the used slides into the discard box and dispersing it over a wide area in the discard box by virtue of the projection, the number of the slides which can be received in the discard box can be increased. Further by disposing the tip drawing station in the vicinity of the incubator and recovering the nozzle tips and the slides in the same discard box, discarding of the tips and the slides are facilitated and handling of the system is facilitated.

DESCRIPTION OF THE PREFERRED EMBODIMENT

Figure 1:
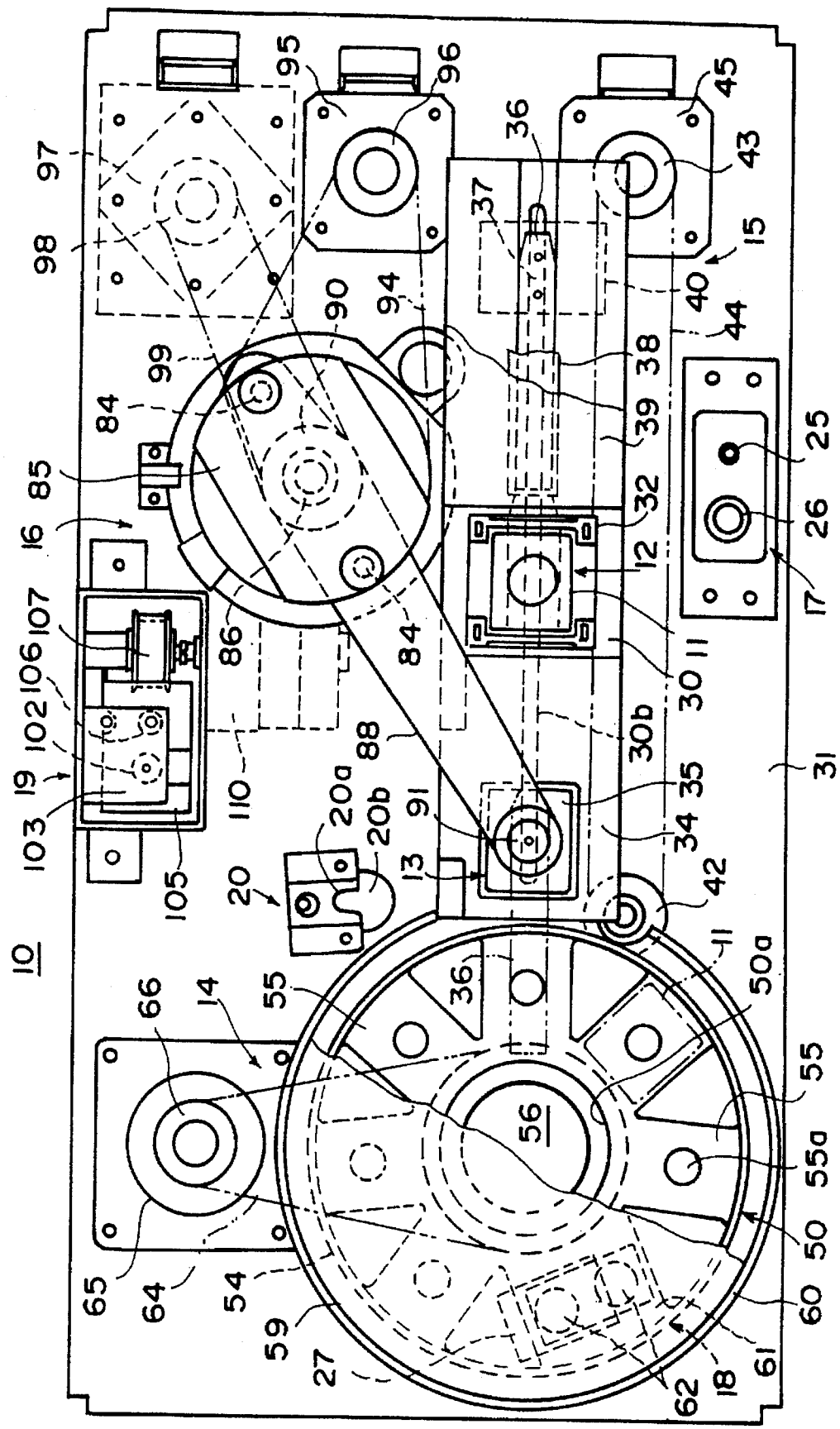
FIG. 1 is a plan view showing an important part of a biochemical analysis system in accordance with an embodiment of the present invention.

In FIG. 1, a biochemical analysis system 10 in accordance with an embodiment of the present invention comprises a slide storage station 12 in which virgin chemical analysis slides 11 are stored, a depositing station 13 at which a sample liquid is deposited on the chemical analysis slide 11 and an incubator 14 which incubates the chemical analysis slides 11 at a predetermined temperature for a predetermined time. A transfer mechanism 15 takes out the chemical analysis slides 11 from the slide storage station 12 one by one and transfers then to the depositing station 13. A depositing mechanism 16 is provided at the depositing station 13. The depositing mechanism 16 has a depositing nozzle 91 and a nozzle tip 25 (FIG. 4) is removably mounted on the depositing nozzle 91. The depositing mechanism 16 sucks, into the nozzle tip 25, sample liquid in a sample cup 26 in a sample feed station 17 and deposits the sample liquid in a predetermined amount on the chemical analysis slide 11 transferred to the depositing station 13. The transfer mechanism 15 loads the chemical analysis slide 11 deposited with the sample liquid in a slide holding portion 55 of the incubator 14. The incubator 14 incubates the slide 11 with the sample liquid at a predetermined temperature for a predetermined time. A light measuring system 18 measures the degree of coloring (reflective optical density) of the slide 11 after the incubation with a light measuring head 27. After the measurement, the transfer mechanism 15 transfers the slide 11 toward the center of the incubator 14 and drops it into a discarding hole 56 which opens at the center of the incubator 14. The depositing mechanism 16 has a syringe mechanism 19 for causing the nozzle tip 25 to suck and discharge the sample liquid and the nozzle tip 25 is removed from the depositing nozzle 91 after each deposition at a tip drawing station 20 near the incubator 14 and is dropped downward to be discarded. The chemical analysis slide 11 comprises a rectangular mount and a reagent layer formed in the mount. A depositing hole and a light measuring hole are formed respectively on the upper and lower sides of the mount.

Figure 2:
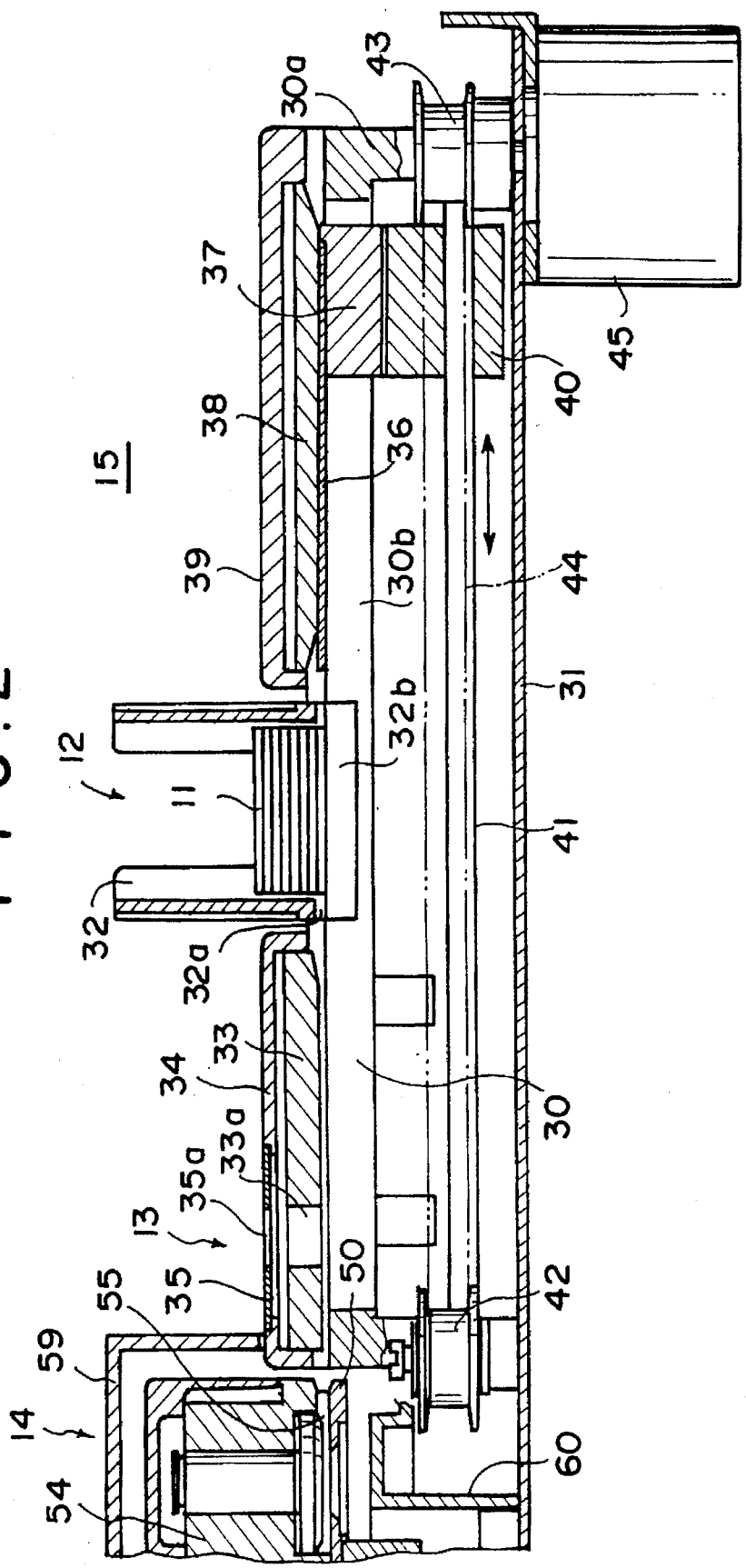
FIG. 2 is a cross-sectional view of the transfer means employed in the biochemical analysis system.

As shown in FIG. 2, the transfer mechanism 15 comprises a transfer table 30 which linearly extends toward the center of the incubator 14. The transfer table 30 has front and rear legs 30a supported on a base 31. The slide storage station 12 is disposed above the transfer table 30 substantially at the middle thereof and the depositing station 13 is disposed above the transfer table 30 between the slide storage station 12 and the incubator 14.

The slide storage station 12 has a slide guide 32 which holds a stack of virgin chemical analysis slides 11. The slide guide 32 is mounted in a recess on the transfer table 30 so that the lowermost slide 11 in the stack is positioned flush with the transfer surface of the transfer table 30. An opening 32a which permits only one slide 11 to pass through the opening 32a is formed on the lower end of the front side of the slide guide 32. An opening which permits an inserter (to be described later) to pass therethrough is formed on the rear side of the slide guide 32 and a groove 32b which communicates with a slit 30b (to be described later) formed in the transfer table 30 is formed in the bottom of the slide guide 32. A cartridge containing therein a stack of chemical analysis slides 11 may be set to the slide guide 32.

A slide holder 33 having therein a circular opening 33a is provided at the depositing station 13 and is housed to be slightly movable up and down in a cover 34 fixed above the transfer table 34. A glass plate 35 is fixed on the cover 34. The glass plate 35 is provided with an opening 35a and the sample liquid is deposited on the slide 11 through the openings 33a and 35a.

The chemical analysis slide 11 is transferred by an inserter 36 in the form of a plate. That is, a slit 30b is formed in the transfer table 30 to extend in the longitudinal direction along the central axis thereof, and the inserter 36 is placed on the transfer table 30 to be slidable along the slit 30b. A block 37 is connected to the lower surface of the rear end portion of the inserter 36 through the slit 30b and is slidable along the slit 30b. A holding plate 38 which holds the inserter 36 is provided on the transfer plate 30 on the rear side of the slide storage station 12 to be slightly movable up and down in a cover 39.

A slider 40 is mounted on the lower side of the block 37. The slider. 40 is supported on a guide rod 41 to be slidable in the longitudinal direction of the transfer table 30. A belt 44 passed around pulleys 42 and 43 is fixed to the slider 40. The pulley 43 is driven by a motor 45 to move the slider 40 fixed to the belt 44. The inserter 36 is moved together with the slider 40 and pushes the lowermost slide 11 of the stack of the chemical analysis slides in the slide guide 32.

The motor 45 is controlled so that the inserter 36 pushes the lowermost slide 11 to the depositing station 13, inserts it into the slide holding portion 55 of the incubator 14 after deposition of a sample liquid and drops it into the discarding hole 56 after measurement.

Figure 3:
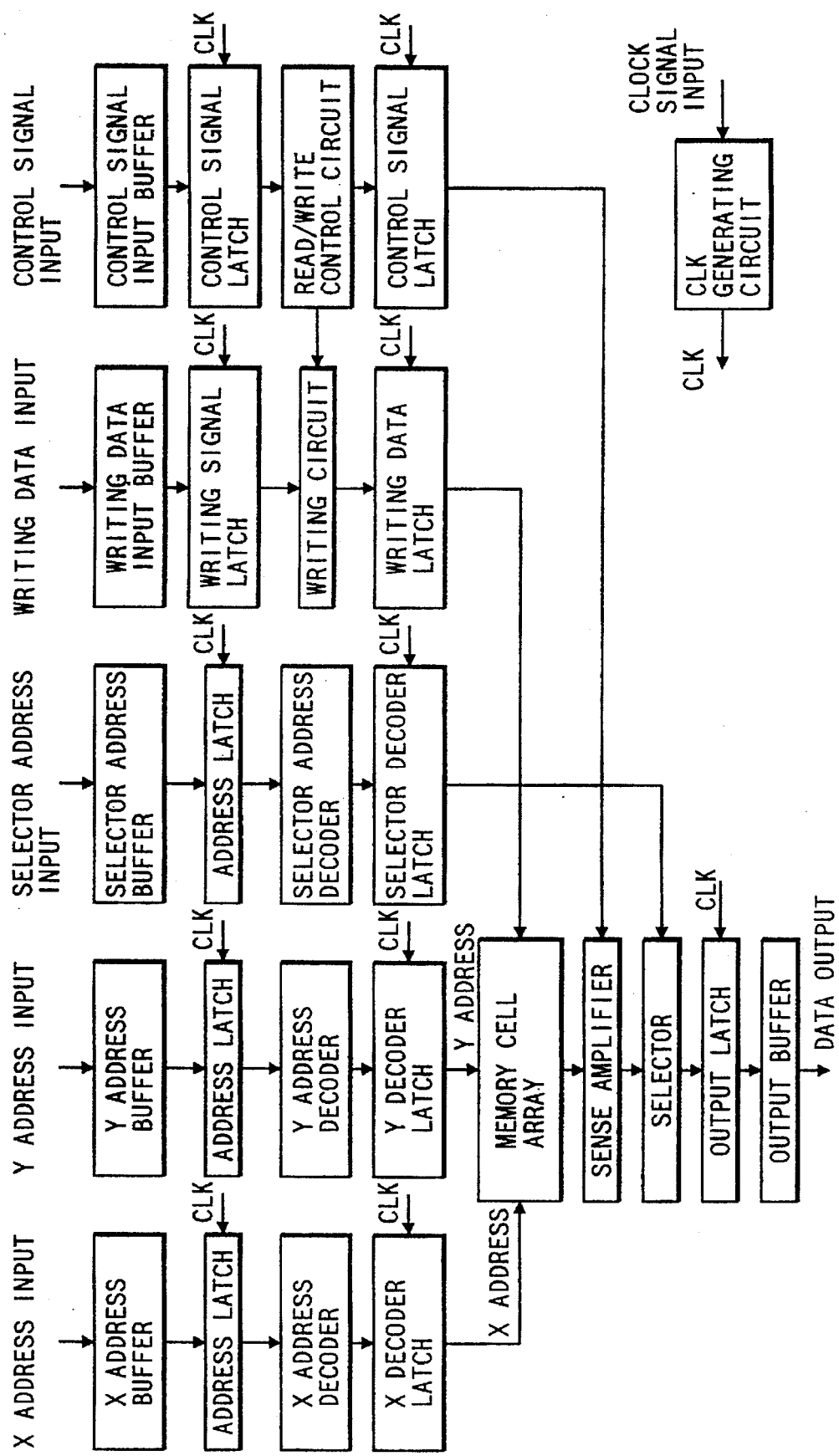
FIG. 3 is a cross-sectional view of the incubator employed in the biochemical analysis system.

As shown in FIG. 3, the incubator 14 comprises a disk-like rotary member 50 supported for rotation by a bearing portion 53 by way of a tubular member 51 fixed to the lower side of the rotary member 50 at the center thereof. A plurality of recesses (e.g., six) are formed on the upper surface of the rotary member 50 at predetermined intervals in the circumferential direction of the rotary member 50. An upper member 54 having a flat lower surface is mounted on the rotary member 50 to form slide holding portions 55 in the form of slits together with the recesses on the upper surface of the rotary member 50. The bottom of each slide holding portion 55 is flush with the transfer surface of the transfer table 30 and the transfer table 30 extends close to the outer peripheral surface of the rotary member 50.

The inside space of the tubular member 51 forms said discarding hole 56 and an opening 50a communicating with the inside space of the tubular member 51 is formed in the rotary member 50 at the center thereof. Each of the slide holding portions 55 communicates with the opening 50a at the inner end thereof so that the slide 11 in the slide holding portion 55 can be dropped into the discarding hole 56 by pushing the slide 11 toward the center of the incubator 14 along the holding portion 55.

The upper member 54 is provided with a heating means (not shown) and the chemical analysis slides 11 in the slide holding portions 55 are held at a predetermined temperature by controlling the heating means. The upper member 54 is further provided with hold-down members 57 which hold down the slides 11 in the respective slide holding portions 55 from above and prevent evaporation of the sample liquids deposited on the slides 11. A cover 58 is provided on the upper member 54. Further the incubator 14 is covered by light-shielding upper and lower covers 59 and 60.

A light measuring opening 55a is formed in the bottom of each slide holding portion 55 at the center thereof, and the light measuring head 27 positioned below the slide holding portion 55 measures the reflective optical density of the chemical analysis slide 11 through the light measuring opening 55a. A reference plate holding portion 61 (FIG. 1) is formed in the rotary member 50 in alignment with the slide holding portions 55 on one circumference. White and black density reference plates 62 for calibration of the light measuring head 27 are provided in the reference plate holding portion 61.

A timing belt 64 is passed around the tubular member 51 and a pulley of a driving motor 65 and the rotary member 50 is rotated back and forth by rotating the motor 65 in opposite directions. The rotary member 50 is rotated in the following manner. That is, the rotary member 50 is first rotated so that the white density reference plate is positioned above the light measuring head 27, where the light measuring head 27 measures the density of the white density reference plate, and then rotated so that the black density reference plate is positioned above the light measuring head 27, where the light measuring head 27 measures the density of the black density reference plate. After thus calibrating the light measuring head 27, the rotary member 50 is rotated so that the chemical analysis slides 11 in the slide holding portions 55 are positioned above the light measuring head 27 one by one, thereby measuring the density of each slide. Thereafter the rotary member 50 is rotated to the original position, where it waits for measurement another sets of slides 11.

Figure 5:
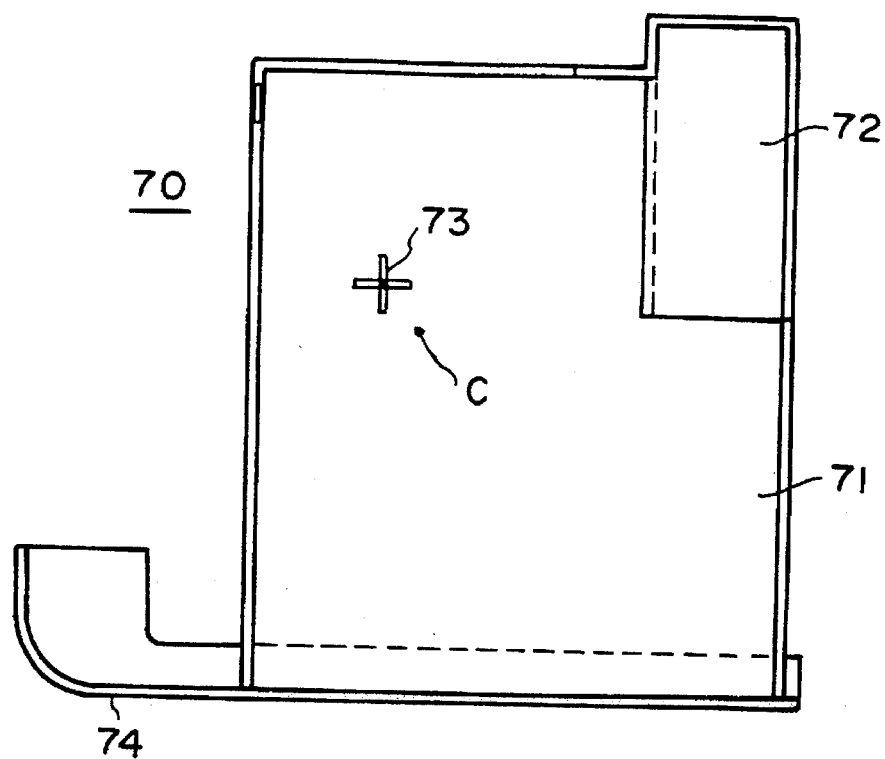
FIG. 5 is a plan view of the discard box employed in the biochemical analysis system.
Figure 6:
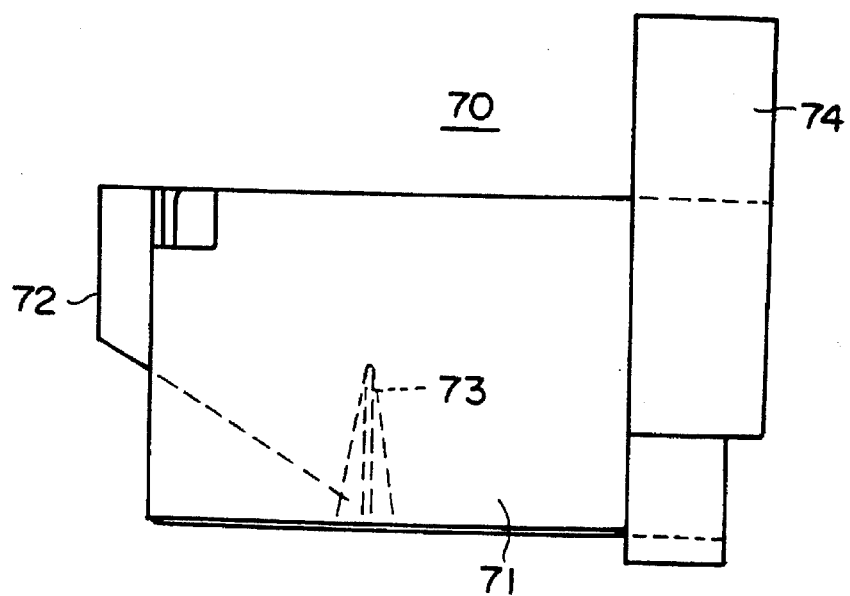
FIG. 6 is a side view of the discard box.

A discard box 70 for recovering the chemical analysis slides 11 after measurement is positioned below the incubator 14. As shown in FIGS. 5 and 6, the discard box 70 a slide chamber 71 below the discarding hole 56 in the tubular member 51. The slide chamber 71 is wide on one side of the center C of the incubator 14 for the reason of layout of the other instruments. A slant portion 72 is formed at one corner of the slide chamber 71 and the nozzle tips 25 which are changed each time the sample liquid is changed is dropped on the slant portion 72. The slant portion 72 is positioned below the tip drawing station 20 and slants downward (20° to 45°) toward the center of the slide chamber 71 so that the nozzle tip 25 dropped on the slant portion 72 is led toward the center of the slide chamber 71.

A projection 73 is projects upward from the bottom of the slide chamber 71 at a portion on a side of the center C of the incubator 14 opposite to the side where the slide chamber 71 is wide. The projection 73 may be like a needle or a ball in shape and causes the chemical analysis slides 11 dropped through the discarding hole 56 to disperse in various directions. A decoration member 74 which is continuous with an outer casing of the biochemical analysis system 10 is provided on the side wall of the slide chamber 71 of the discard box 70.

Figure 4:
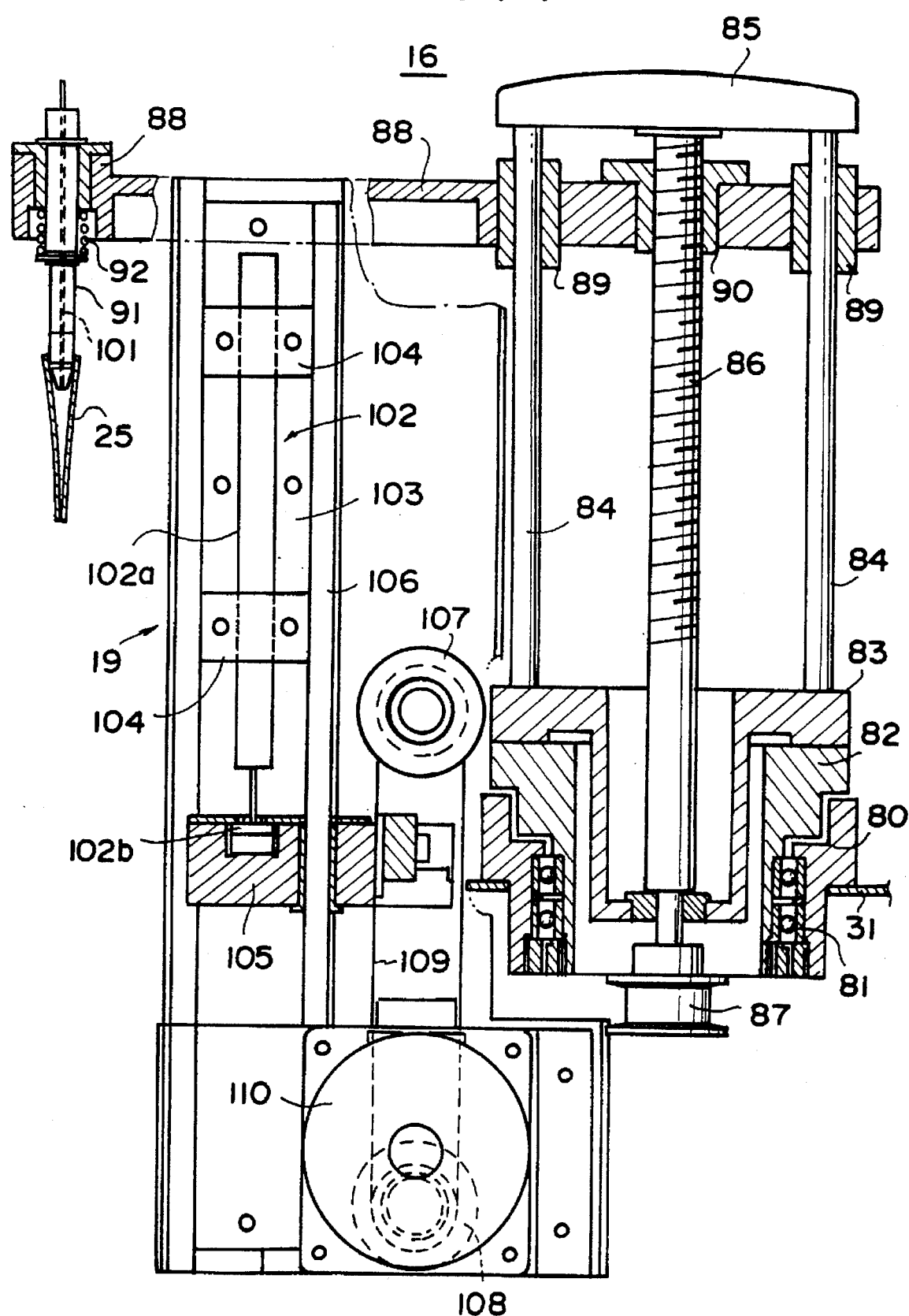
FIG. 4 is a cross-sectional view of the depositing means employed in the biochemical analysis system.

As shown in FIG. 4, the depositing mechanism 16 comprises a rotary base 82 which is supported for rotation on a support member 80 by way of a bearing 81. The support member 80 is mounted on the base 31. A flange member 83 is mounted on the top of the rotary base 82 to be rotated together with the rotary base 82. A pair of guide rods 84 extend upward in parallel to each other from the flange member 84 at portions near the outer edge of the flange member 84 and the upper ends of the respective guide rods 84 are fixed to a connecting member 85. A lead screw 86 is supported for rotation by the connecting member 85 at the lower end thereof. The lead screw 86 is further supported for rotation by the flange member 83 at a lower end portion thereof. The lower end portion of the lead screw 86 extends through the flange member 83 and a pulley 87 is fixed to the lower end of the lead screw 86. A depositing arm 88 is slidably supported by the guide rods 84 at its base end portion by way of sleeves 89. A nut member 90 is fixedly fitted in an opening formed in the base end portion of the depositing arm 88 and is in mesh with the lead screw 86 so that the depositing arm 88 is moved up and down along the guide rods 84 in response to rotation of the lead screw 86.

The depositing nozzle 91 extends in the vertical direction through the free end portion of the depositing arm 88. The depositing nozzle 91 is supported by the arm 88 to be slidable up and down at its shank portion and is urged downward by a spring 92. As described above, a nozzle tip 25 is removably mounted on the nozzle 91. That is, virgin nozzle tips are prepared in the sample feed station 17 and a nozzle tip 25 is fitted on the nozzle 91 in response to downward movement of the arm 88. After use, the nozzle tip 25 is removed from the nozzle 91 by moving upward the arm 88 with the upper end of the tip 25 in engagement with an engagement notch 20a formed in the tip drawing station 20 and is dropped into the discard box 70 through an opening 20b formed in the tip drawing station 20.

The depositing arm 88 is swung by a driving mechanism comprising a timing belt 94 (FIG. 1) passed around the rotary base 82 (or the flange member 83) and a driving pulley 96 of a swinging motor 95. The depositing arm 88 is moved up and down or the lead screw 86 is rotated in one direction and the other by a driving mechanism comprising a belt 96 (FIG. 1) passed around the pulley 87 fixed to the lower end of the lead screw 86 and a driving pulley 98 of an up-and-down motor 97 (FIG. 1).

An air passage 101 extends through the depositing nozzle 91 and opens at the lower end of the nozzle 91. An air pipe (not shown) is connected to the upper end of the air passage 101 at one end and to a syringe 102 of the syringe mechanism 19. The syringe 102 comprises a cylinder 102a in which a piston (not shown) is slidably received. The cylinder 102a is fixedly supported by a support column 103 by way of retainers 104. The outer end 102b of a rod connected to the piston at the inner end thereof is connected to an up-and-down member 105 which is movable up and down along a guide rod 106. A belt 109 is fixed to one end of the up-and-down member 105 and is passed around upper and lower pulleys 107 and 108. A syringe motor 110 is connected to the lower pulley 108 so that the belt 109 is driven by the syringe motor 110 to move the up-and-down member 105, thereby supplying vacuum or air pressure to the nozzle 91. That is, when the up-and-down member 105 is moved downward with the nozzle tip 25 dipped into the sample liquid in the sample cup 26, the sample liquid is sucked into the nozzle tip 25. Then the depositing mechanism 16 swings the nozzle 91 to the depositing station 13 and deposits the sample liquid in a predetermined amount by moving upward the up-and-down member 105. The nozzle tip 25 and the sample cup 26 in the sample feed station 17, the depositing station 13 and the tip drawing station 20 are all positioned along the swinging path of the nozzle 91.

As can be understood from the description above, in the biochemical analysis system 10 of this embodiment, the chemical analysis slides 11 are removed from the incubator 14 after measurement by pushing them toward the center of the incubator 14 by the transfer mechanism 15 which loads them in the incubator 14 and accordingly loading and removal of the chemical analysis slides 11 can be effected by the same transfer mechanism. Further since the slides 11 are transferred along a linear path and the transfer mechanism may gain access to the incubator 14 in a single position, the transfer mechanism may be simple in structure and transfer of the slides can be effected with high reliability.

Further, by recovering the used slides 11 into the discard box 70 and dispersing it over a wide area in the discard box 70 by virtue of the projection 73, the number of the slides 11 which can be received in the discard box 70 can be increased. Further by disposing the tip drawing station 20 in the vicinity of the incubator 14 and recovering the nozzle tips 20 and the slides 11 in the same discard box 70, discarding of the tips 25 and the slides 11 are facilitated and handling of the system is facilitated. In addition to these facts, in accordance with the embodiment described above, by efficiently laying out the incubator 14, the transfer mechanism 15 and the depositing mechanism 16, a compact biochemical analysis system can be obtained.

The number of the slide holding portions 55 in the incubator 14 need not be limited to a particular value. Further, a plurality of sample cups 26 may be disposed side by side along the swinging path of the nozzle 91 in order to improve the processing efficiency, or instead a sample tray carrying thereon a plurality of sample cups 26 may be fed so that the sample cups 26 are positioned in a predetermined position one by one.

What is claimed is:

1. A biochemical analysis system, comprising:

a depositing means for depositing a sample liquid on a chemical analysis slide having a reagent layer;

an incubator for incubating the chemical analysis slide with the sample liquid at a predetermined temperature for a predetermined time;

a common transfer means for transferring the slide from a slide storage station to a predetermined station in the incubator and for thereafter transferring the slide from said predetermined station;

an optical density measuring means for measuring the optical density of the chemical analysis slide after incubation and determining the concentration of a specific biochemical component in the sample liquid through the optical density of the chemical analysis slide; and a discard box including a chamber and having an inclined side wall at least partially defining said chamber, wherein said incubator has a rotary body in which a slide discarding hole is formed at the center thereof and a plurality of slide holding portions are formed to extend from the outer peripheral surface of the rotary body toward the center of the rotary body and communicate with the slide discarding hole, said transfer means inserts the chemical analysis slides into the respective slide holding portions by moving each slide from said slide storage station toward the center of the rotary body and drops the slides into the discarding hole after measurement by moving the slides further toward the center of the rotary body and wherein said depositing means is disposed along said transfer means between said slide storage station and said predetermined station and wherein said depositing means includes a nozzle tip for sucking and discharging the sample liquid, a tip drawing means disposed proximate the incubator for removing the nozzle tip from the depositing means, the nozzle tips being discarded into the discard box above said inclined side wall so as to be deflected into said chamber and wherein said discard box is disposed below the discarding hole for recovering the used slides and a projection is provided in the discard box in vertical alignment with the discard hole such that the dropped slides contact the projection and are dispersed into the discard box, said projection having one of a needle shape and a ball shape and wherein said discard box includes a first section disposed below the slide discarding hole and a second section which is wider than said first section disposed adjacent thereto, wherein the projection is disposed at a position displaced from a center of the slide discarding hole in a direction that is opposite said second section and opposite said inclined sidewall.

2. The biochemical analysis system of claim 1, wherein said rotary body is devoid of any structure in said slide discarding hole so that said slides can fall freely into said discarding hole.

3. The biochemical analysis system of claim 1, wherein said rotary body includes a tubular member extending downwardly therefrom, said slide discarding hole extending through said tubular member.

4. A biochemical analysis system as defined in claim 1, wherein said inclined side wall is inclined an angle between 20° and 45°.

5. The biochemical analysis system of claim 1, wherein said transfer means includes a transfer table which linearly extends towards said slide discarding hole.

6. The biochemical analysis system of claim 5, further comprising a slide supply station disposed directly above said transfer table for supplying virgin slides to said transfer table.

7. The biochemical analysis system of claim 6, wherein said depositing means is disposed above said transfer table between said slide storage station and said incubator.

* * * * *